(12) United States Patent
Antunes Barros et al.

(10) Patent No.: US 12,728,029 B2
(45) Date of Patent: Sep. 8, 2026

(54) MEDICAL DEVICE FOR COLLECTION AND RELEASE OF BODILY WASTE FROM A SUBJECT, USES AND METHOD THEREOF

(71) Applicants: Association for the Advancement of Tissue Engineering and Cell Based Technologies & Therapies (A4tec) Associacao, Guimarães (PT); Hydrumedical, S.A., Barco (PT); Triple IDEA, LDA, Galegos (PT)

(72) Inventors: Alexandre António Antunes Barros, Caldas Das Taipas (PT); Catarina Pires Sepúlveda, Braga (PT); Liliana Patrícia Sousa Gonçalves Dos Reis, Moreira de Cónegos (PT); Sara Carvalheira Neves, Braga (PT); Rui Luís Gonçalves Dos Reis, Oporto (PT); André Manuel Macedo Santos, Galegos (PT); Daniela Torres Cardoso, Galegos (PT); André Torres Cardoso, Galegos (PT)

(73) Assignees: Association for the Advancement of Tissue Engineering and Cell Based Technologies & Therapies, Associação (PT); Hydrumedical, S.A., Barco (PT); Triple IDEA, LDA, Galegos (Santa Maria) (PT)

( * ) Notice: Subject to any disclaimer, the term of this patent is extended or adjusted under 35 U.S.C. 154(b) by 564 days.

(21) Appl. No.: 18/248,977

(22) PCT Filed: Oct. 13, 2021

(86) PCT No.: PCT/IB2021/059413
§ 371 (c)(1),
(2) Date: Apr. 13, 2023

(87) PCT Pub. No.: WO2022/079634
PCT Pub. Date: Apr. 21, 2022

(65) Prior Publication Data

US 2023/0414398 A1 Dec. 28, 2023

(30) Foreign Application Priority Data

Oct. 13, 2020 (PT) ........................................ 116822
Dec. 29, 2020 (EP) .................................... 20217714

(51) Int. Cl.
*A61F 5/441* (2006.01)
*A61F 5/445* (2006.01)

(52) U.S. Cl.
CPC .............. *A61F 5/441* (2013.01); *A61F 5/445* (2013.01); *A61F 2005/4415* (2013.01)

(58) Field of Classification Search
CPC .. A61F 5/441; A61F 5/445; A61F 2005/4415; A61F 5/4405
See application file for complete search history.

(56) References Cited

U.S. PATENT DOCUMENTS 5,372,594 A 12/1994 Colacello et al.
5,401,264 A 3/1995 Leise, Jr.
(Continued)

FOREIGN PATENT DOCUMENTS

EP 1774932 A1 4/2007

OTHER PUBLICATIONS

International Search Report and Written Opinion for corresponding PCT Application No. PCT/IB2021/059413 dated Feb. 10, 2022 (11 pages).

(Continued)

*Primary Examiner* — Catharine L Anderson
*Assistant Examiner* — Hans Kaliher
(74) *Attorney, Agent, or Firm* — Leason Ellis LLP

(57) ABSTRACT

The present disclosure relates to an ostomy device for manually controlling the release and collection of bodily
(Continued)

waste from an external stoma of a subject. The ostomy device includes a collapsible collecting bag; a first base plate for encircling the stoma; a second base plate having an opening and connected to the collecting bag such that bodily waste can flow through the first base plate and the opening of the second base plate into the collecting bag; a valve for releasing intra-abdominal gas into an exterior of the device; and a cap for closing and for opening the device comprising an inward side for closing onto the second base plate. The valve comprises a valve member for closing the valve, which is openable by pressure applied in a direction towards the subject skin. The present disclosure also relates to an ostomy system including the aforesaid medical device.

18 Claims, 7 Drawing Sheets

(56) References Cited

U.S. PATENT DOCUMENTS

2012/0179124 A1* 7/2012 Nguyen-Demary .... A61F 5/448 604/335
2013/0053802 A1 2/2013 Maidl et al.
2016/0166424 A1* 6/2016 Hanuka .................. A61F 5/445 604/335
2017/0360592 A1* 12/2017 Carrubba ................ A61F 5/445
2017/0367871 A1* 12/2017 Dinakara ................ A61F 5/445
2019/0133812 A1* 5/2019 Seres ...................... A61F 5/443
2022/0133522 A1* 5/2022 Chopra .................. A61F 5/448 604/335

OTHER PUBLICATIONS

Anonymous, "Access to Ostomy Supplies and Innovation: Guiding Principles for European Payers", Eucomed Medical Technology, Sep. 20, 2012 (19 pages).
Anonymous, "New Ostomy Patient Guide", United Ostomy Associations of America, Inc., Jan. 2017.

* cited by examiner

MEDICAL DEVICE FOR COLLECTION AND RELEASE OF BODILY WASTE FROM A SUBJECT, USES AND METHOD THEREOF

CROSS-REFERENCE TO RELATED APPLICATIONS

This application is a U.S. National Stage Application under 35 U.S.C. § 371 of International Patent Application No. PCT/IB2021/059413, filed Oct. 13, 2021, which claims priority to Portugal Patent Application No. 116822, filed Oct. 13, 2020, and EP patent application No. 20217714.3, filed Dec. 29, 2020, the contents of which are each hereby incorporated by reference in their respective entireties.

TECHNICAL FIELD

The present disclosure relates to a medical device for controlling the release of waste from a surgically diverted biological system in ostomized patients.

BACKGROUND

Ostomy surgery is a life-saving procedure that can be necessary in different scenarios, such as birth defects, cancer, inflammatory bowel disease, diverticulitis, incontinence, severe abdominal trauma, among others. Briefly, this procedure diverts the bodily waste, forcing it to pass through a surgically created stoma, located at the abdomen. Then, the bodily waste is discharged into a prosthetic pouch located outside the body. The most common ostomies are colostomy, urostomy and ileostomy.

Colostomy consists of a surgical procedure in which a cross section of the colon is performed, with the anal region being sutured and closed, while the other portion is anastomosed to the abdominal wall.

After surgery, it is mandatory that the patient uses a colostomy bag for waste collection. According to the ostomy procedure, temporary or definitive, the patient is submitted to, they may have to use the colostomy bag temporarily or "ad eternum". Invariably, there are several personal, intimate, social and professional aspects that change during this process. A colostomized patient loses control over his/her body, namely flatulence and stool output, carrying innumerable physical and psychological problems and limitations, whose severity will depend on patient resilience.

Worldwide, the real prevalence of the problem is impressive. Just in the United States of America (USA) and according to the "United Ostomy Associations of America", there are over 750.000 Americans with at least one kind of stoma—36.1% (270.000) with colostomy and 32.3% (242.000) with ileostomy. Also, in the USA, there are over 100.000 new ostomy surgeries, every single year.

In Portugal, the estimated number of ostomized patient is between 10.000 to 12.000, while in the European Union (UE) there are nearly 700.000 (RTP, 2015) (Eucomed-Medical Technology, 2012 a) (Eucomed-Medical Technology, 2012 b). The studies analysed do not allow the precise indication of the number of colostomized patients in Portugal or internationally, but they provide an elucidative perspective over the relevance of this health problematic.

Waste collecting systems are responsible for managing the main ostomies problem: bodily waste collection. Therefore, there has been a great effort from manufacturers to improve some of the products features: gas filters, fixation system and some other small details. Nevertheless, only small changes have been performed, keeping the overall concept untouched. In a general way, there has been an incredible evolution in medical devices in the past few years, accompanying the technology available. Colostomy' related devices, despite great scientific effort to try to come up with alternatives to colostomy bags, namely artificial sphincters and occluded systems, have not yet find a truly effective alternative until now.

These facts are disclosed in order to illustrate the technical problem addressed by the present disclosure.

GENERAL DESCRIPTION

The present disclosure relates to a medical device for controlling the release of bodily waste in ostomized patients, destined to all the patients that, for some reason, have been submitted to an ostomy. The ostomy bag will no longer have to be visible, allowing the control over gas and stool release to the moment and the place the patient chooses it to be the most suitable, avoiding uncomfortable noises and smells.

This non-invasive device, besides allowing a significant life quality improvement to its user, also allows greater autonomy, freedom and intimacy preservation.

In an embodiment, this device is a long-term device, reusable, totally washable, and/or use sterilizable product, and represents an improvement comparing to other available products on the market.

In an aspect, the present disclosure relates to an medical ostomy device for manually controlling the release and collection of bodily waste from an external stoma of an ostomized subject, comprising a collapsible collecting bag; a first base plate for encircling the stoma and for placing directly on the skin, i.e., the subject skin, that surrounds the stoma; a second base plate having an opening and connected to the collecting bag such that bodily waste can flow through the first base plate and the opening of the second base plate (3) into the collecting bag; a valve for releasing intra-abdominal gas into an exterior of the device; and a cap for closing and for opening the device comprising an inward side for closing onto the second base plate; wherein the valve comprises a valve member for closing said valve, which is openable by pressure applied in a direction towards the subject skin. For the scope of the present disclosure, a direction towards the subject skin is defined as a direction substantially perpendicular to the subject skin.

In an embodiment, the valve member is a flexible membrane having a slit which is openable by pressure applied by a hand or a finger of the subject, in a direction towards the subject skin.

In an embodiment, the cap is manually removable from the second base plate.

In an embodiment, the valve member is arranged to be openable by the applied pressure to release intra-abdominal gas into the exterior of the device when the cap is closed onto the second base plate. Specifically, the valve member is arranged to be openable by the applied pressure to release intra-abdominal gas into the exterior of the device independently of the cap being closed onto the second base plate.

In an embodiment, the valve member is a flexible membrane having a slit which is openable by pressure applied in the direction towards the skin that surrounds the stoma.

In another embodiment, the valve member is a flexible membrane having a slit which is openable by pressure of gas generated by internal physiological activity of the subject, such as the rhythmic contractions of the digestive tract (peristalsis).

In an embodiment, the valve comprises a degassing aperture comprising: a first channel for gas flow from the stoma through the first base plate; said valve member for gas flow from the first channel; and a second channel for gas flow from said valve member through the second base plate into the exterior.

In an embodiment, the first channel is arranged to be placed in parallel to the subject skin and the second channel is arranged to be placed perpendicularly to the subject skin.

In an embodiment, the degassing aperture comprises an elastomeric barrier.

In an embodiment, the collecting bag comprises a first end with an opening attached to an outward side of the second base plate and a second end attached to the inward side of the cap for expanding the collecting bag when the cap is manually removed from the second base plate.

In an embodiment, the cap piece is fastenable to the second base plate by a screw thread.

In an embodiment, the collapsible collecting bag is foldable.

In an embodiment, the folds of the folded collecting bag loosen upon cap manual removal, or upon bodily waste release from the stoma, for expediting the fill of the collecting bag.

In an embodiment, the folded compact collecting bag is fold-out by pressure variation between the stoma and the collecting bag.

In an embodiment, the collecting bag is folded in an accordion folding configuration, twisted accordion folding configuration, zig-zag folding configuration, folded perpendicularly and longitudinally to the length axis of the bag, or crumpled.

In an embodiment, the first and second base plates comprise an inlet aperture for fitting in the stoma.

In an embodiment, the first base plate comprises a skin-contacting face for surrounding the stoma.

In an embodiment, said skin-contacting face comprises a sponge, a gaze, a cotton, or combinations thereof, among others.

In an embodiment, the first and second base plates of the ostomy device are attachable by a flange, a screw thread, a snap-fit mechanism or combinations thereof.

In an embodiment, the collapsible collecting bag is an ostomy bag. In another embodiment, the collapsible collecting bag is a colostomy bag, an ileostomy bag, a urostomy bag, a trachea bag, or combinations thereof, among others.

In an embodiment, the collapsible collecting bag is a compact ostomy bag. In another embodiment, the collapsible collecting bag is a compact colostomy bag, a compact ileostomy bag, a compact urostomy bag, a compact trachea bag, or combinations thereof.

In an embodiment, the collapsible collecting bag is disposable and/or biodegradable.

In an embodiment, the collecting bag is lockable by rotation between the second base plate and the cap.

In an embodiment, the collecting bag is attached to the second base plate by heat sealing, suitable glue, a magnetic system, a snap-fit mechanism, an adhesive, ultrasound or combinations thereof.

In another embodiment, the collecting bag is attached to the cap by heat sealing, a suitable glue, a magnetic system, a snap-fit mechanism, an adhesive, ultrasound, or combinations thereof.

In an embodiment, the intersection between the collecting bag and the second base plate is a circle or a convex polygon.

In an embodiment, said ostomy device may comprise a pressure sensor for determining the intra-abdominal pressure of the ostomized subject, an alert system, a power source, and data processor able to monitor the intra-abdominal pressure. Preferably, the data processor is able to activate the alert system when the pressure is equal or superior to a pre-determined threshold.

In an embodiment, the pressure threshold is at least 120 mm Hg, preferably between 5-90 mm Hg, more preferably is at least 15-80 mm Hg, even more preferably is at least 20-60 mm Hg.

In a further embodiment, said ostomy device further comprises a temperature sensor, a gas sensor, or combinations thereof.

In an embodiment, the first base plate is attachable to the body skin by an adhesive layer.

In an embodiment, the bodily waste is a body fluid, in particular intestinal content, more in particular solid (stool), liquid or gaseous (flatus) intestinal content.

In an embodiment the base plates, the valve and the cap of the ostomy device are made of a suitable polymer, in particular polyethylene (PE), polyoxymethylene (POM), VERSAFLEX™ thermoplastic elastomer, polyesters, polyamide, polyurethane, polyethylene copolymers, silicone, or mixtures thereof.

Another aspect of the present disclosure relates to an ostomy system comprising the medical device described in any of the previous embodiments. In particular, the ostomy system is a colostomy pouch, an ileostomy pouch, an urostomy pouch, a trachea pouch, or combinations thereof.

BRIEF DESCRIPTION OF THE DRAWINGS

The following figures provide preferred embodiments for illustrating the description and should not be seen as limiting the scope of disclosure.

DETAILED DESCRIPTION

Figure 1:
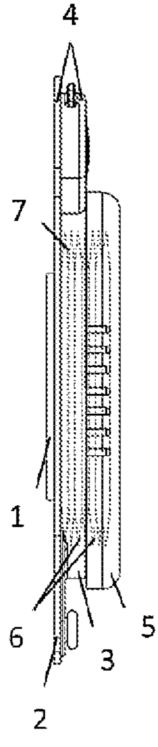
FIG. 1 shows a schematic representation of a lateral view of an embodiment of the complete ostomy device, in a closed configuration, for controlling the release of bodily waste content in ostomized patients.

The present disclosure relates to an ostomy device for manually controlling the release and collection of bodily waste from an external stoma 10 of a subject, comprising: a collapsible collecting bag 7; a first base plate 2 for encircling the stoma 10 and for placing directly on the subject skin that surrounds the stoma 10; a second base plate 3 having an opening and connected to the collecting bag 7 such that bodily waste can flow through the first base plate 2 and the opening of the second base plate 3 into the collecting bag 7; a valve 4 for releasing intra-abdominal gas into an exterior of the device; and a cap 5 for closing and for opening the device comprising an inward side for closing onto the second base plate 3; wherein the valve 4 comprises a valve member 12 for closing said valve, which is openable by pressure applied in a direction towards the subject skin.

It is disclosed an ostomy device for manually controlling the release and collection of bodily waste from an external stoma 10 of a subject, comprising:

- a collapsible collecting bag 7;
- a first base plate 2 for encircling the stoma 10 and for placing directly on the subject skin that surrounds the stoma 10;
- a second base plate 3 having an opening and connected to the collecting bag 7 such that bodily waste can flow through the first base plate 2 and the opening of the second base plate 3 into the collecting bag 7;
- a valve 4 for releasing intra-abdominal gas into an exterior of the device; and a cap 5 for closing and for opening the device comprising an inward side for closing onto the second base plate 3;
- wherein the valve 4 comprises a valve member 12 for closing said valve, wherein the valve member 12 is a flexible membrane having a slit which is openable by pressure applied by a hand or a finger of the subject, in a direction towards the subject skin.

In an embodiment, the collecting bag 7 comprises a first end with an opening attached to an outward side of the second base plate 3 and a second end attached to the inward side of the cap 5 for expanding the collecting bag 7 when the cap 5 is manually removed from the second base plate 3.

In an embodiment, the device of the present disclosure is totally waterproof, washable and non-invasive. It is composed by an exterior component comprising two base plates 2, 3 and a cap 5 that encloses a collapsible collecting bag 7.

In an embodiment, the device of the present disclosure is fixed to the body through an adhesive layer, like the ones already existing in the market, therefore preventing the release of faeces, gases and smells in an uncontrolled way. Its fixing point occurs over the abdominal wall, around the stoma 10, and does not require any extra surgical intervention.

In an embodiment, inside the device of the present disclosure there is the collapsible collecting bag 7. In a closed state, i.e., before release and collection of bodily waste, the collecting bag is in a compacted configuration within the second base plate 3 and the cap piece 5.

FIG. 1 shows a lateral view of an embodiment of the ostomy device. The device is placed in around the stoma, placing the stoma inside an existing inlet aperture 1 on the first base plate 2. The first base plate 2 is attached to the second base plate 3, making the valve 4 in its assembled configuration. The second base plate 3 is additionally attached to the cap 5, by means of a screw thread 6. The collapsible collecting bag 7 is placed between the second base plate 3 and the cap piece 5, in direct contact with the stoma via the inlet aperture 1. In the present embodiment, the collecting bag 7 is folded in an accordion configuration.

Figure 2A:
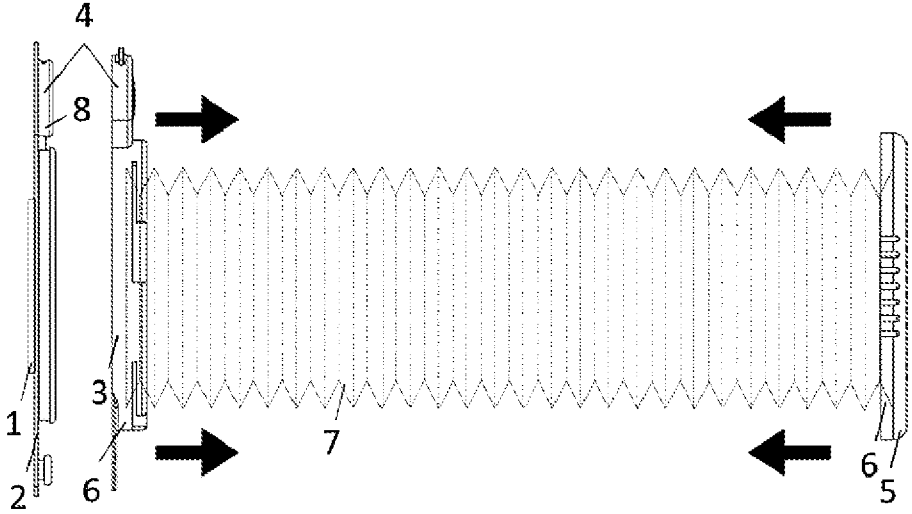
FIG. 2 shows a schematic representation of a lateral view of an embodiment of the ostomy device in an opened configuration.
Figure 2B:
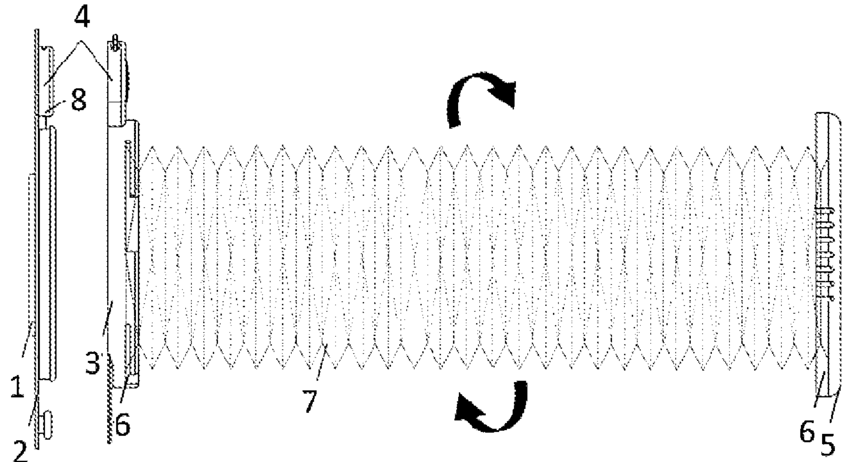

FIG. 2 shows a lateral view of an embodiment of the ostomy device, in an opened configuration. The collecting bag 7 is extended from the second base plate 3 to the cap piece 5. In this embodiment, the foldable collecting bag is folded in an accordion configuration (FIG. 2-A), that can be twisted clockwise or anti-clockwise relative to the bag's longitudinal axis (FIG. 2-B).

Figure 3:
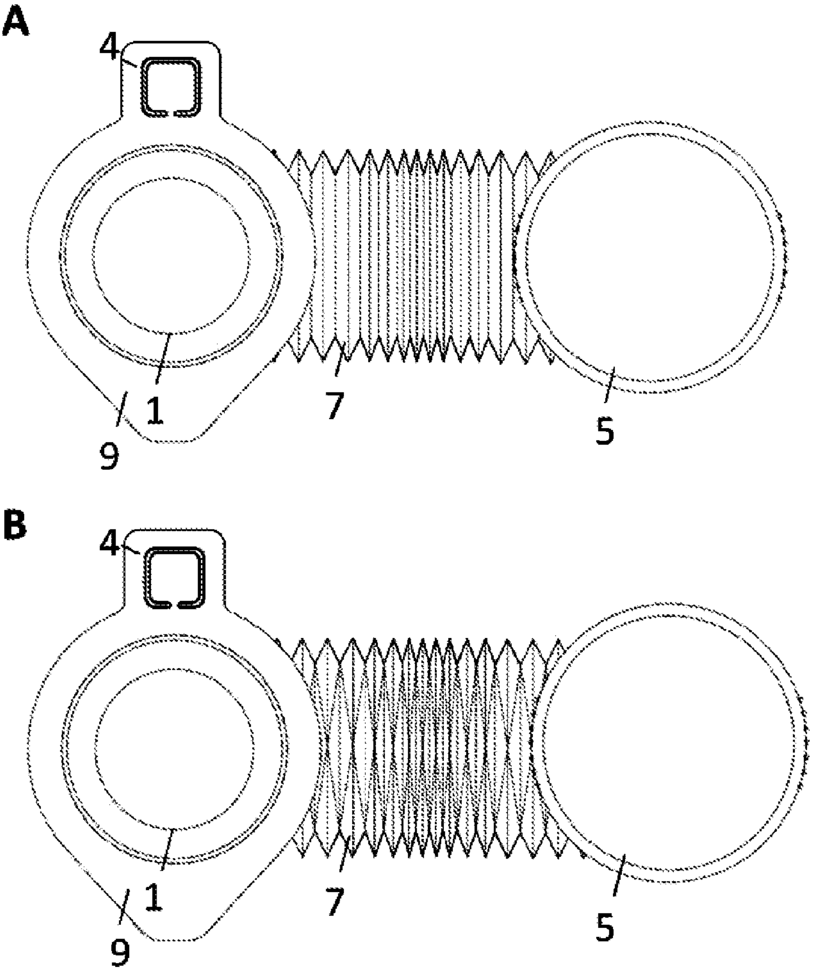
FIG. 3 shows a schematic representation of an embodiment of a top view of the base plate assembly and the cap of the ostomy device.

FIG. 3 shows a schematic representation of an embodiment of a top view of the cap 5 and the base plate assembly 9. The base plate assembly comprises the first and the second base plates 2, 3 and the inlet aperture 1 that is placed around the stoma. The collecting bag 7 can be folded in an accordion (FIG. 3A) or twisted accordion (FIG. 3B) configuration.

Figure 4:
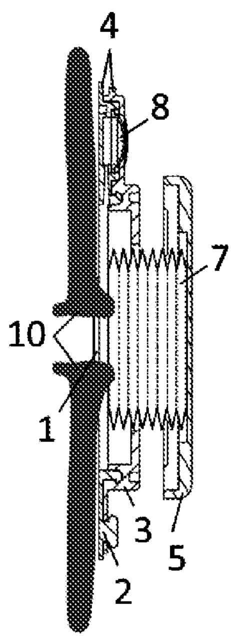
FIG. 4 shows a schematic representation of an embodiment of the application of the ostomy device in a stoma.

FIG. 4 shows a schematic representation of an embodiment of the application of the ostomy device in a stoma 10 wherein a degassing aperture 8 connects the stoma and the external environment of the medical device, making possible the release of gases from the stoma to the environment.

Figure 5:
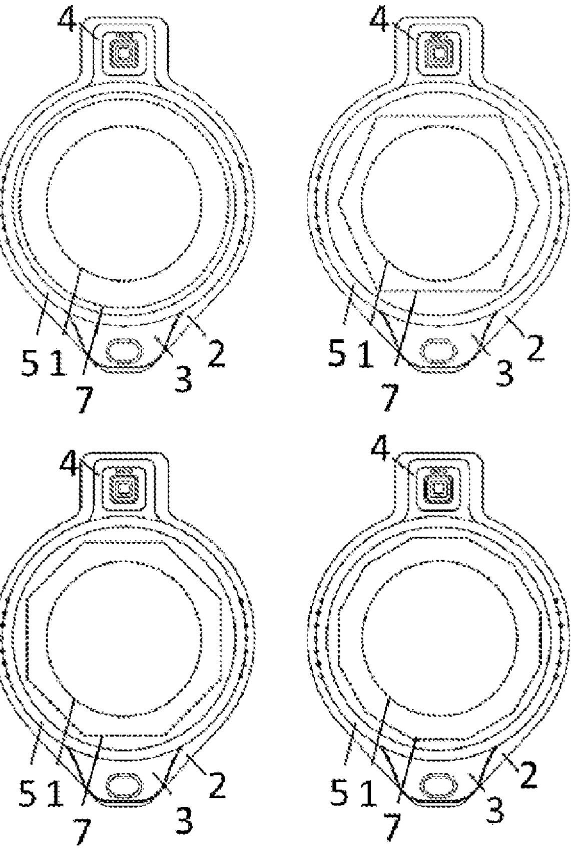
FIG. 5 shows a schematic representation of an embodiment of a front view at the cross-section of the second base plate and the collecting bag, wherein the collecting bag has different cross-sectional geometries.

In an embodiment, the collecting bag has different cross-sectional geometries (FIG. 5), such as a circle or a convex polygon. In another embodiment, the intersection between the collecting bag 7 and the second base plate 3 is a circle or a convex polygon, as depicted in FIG. 5.

When the medical device is manually opened, the collecting bag 7 extends to accommodate the released bodily waste. In an embodiment, the collecting bag 7 is lockable by rotation between the second base plate 3 and the cap 5. In a further embodiment, the collecting bag 7 is unfolded by manual rotation of the cap screw thread 6.

To remove the filled collecting bag, the ostomized patient just needs to disassemble the second base plate 3 from the first base plate 2.

In an embodiment, if there are faeces inside the device, the user just has to open the cap piece 5. Due to pressure variation, the folded compact collecting bag 7, that is comprised within the second base plate 3 and the cap piece 5 inside the equipment, expands and is filled with faecal content. In a further embodiment, once the release is over, the user removes the bag component 7, does the sanitation and substitutes the collecting bag 7 by a new one.

Figure 6A:
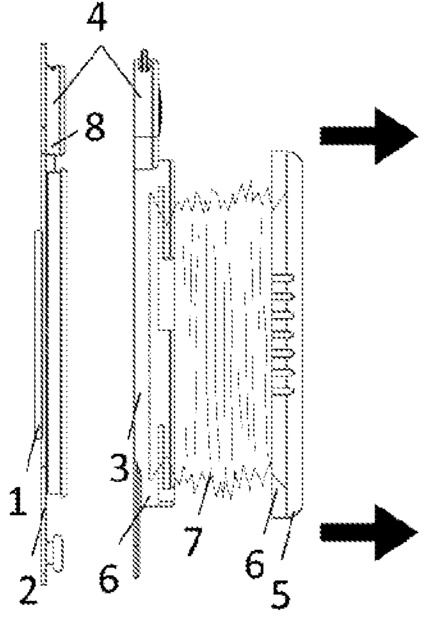
FIG. 6 shows a schematic representation of an embodiment of the ostomy device wherein the foldable collecting bag is crumpled between the second base plate and the cap piece in a closed (FIG. 6A) and opened (FIG. 6B) configuration.
Figure 6B:
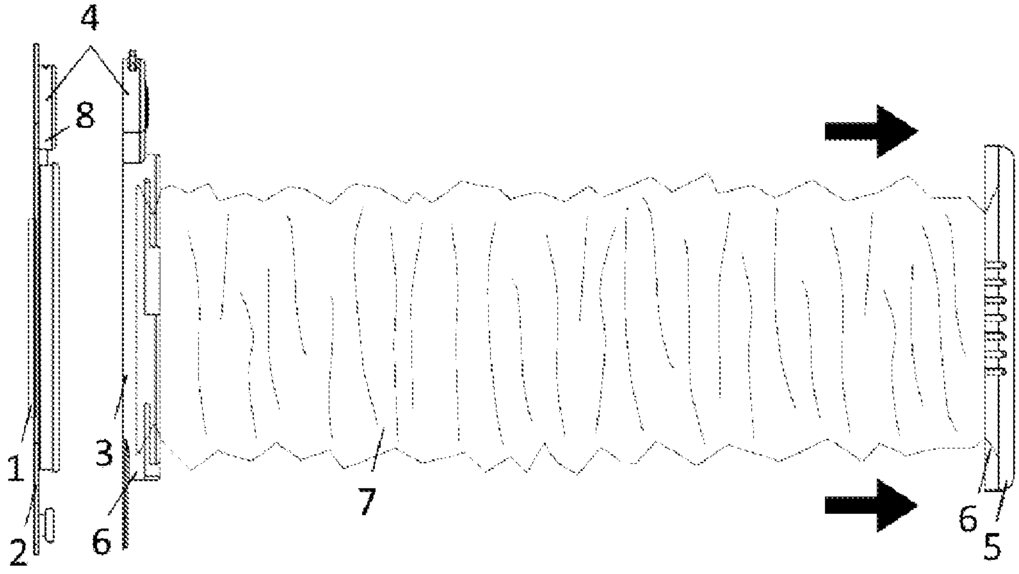
Figure 7A:
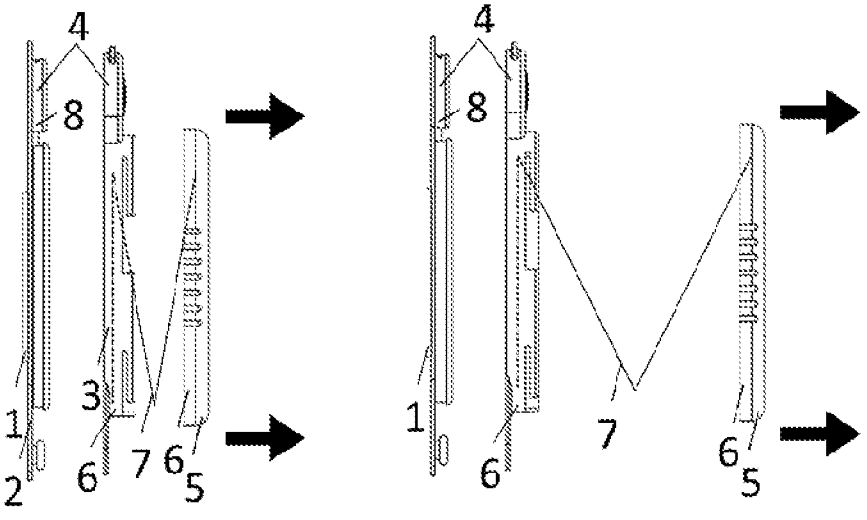
FIG. 7 shows a schematic representation of an embodiment of the ostomy device wherein the foldable collecting bag is folded between the second base plate and the cap piece, in a zig-zag folding (FIGS. 7A and 7B) or a folding perpendicularly and longitudinally to the length axis of the bag (FIGS. 7C and 7D).
Figure 7B:
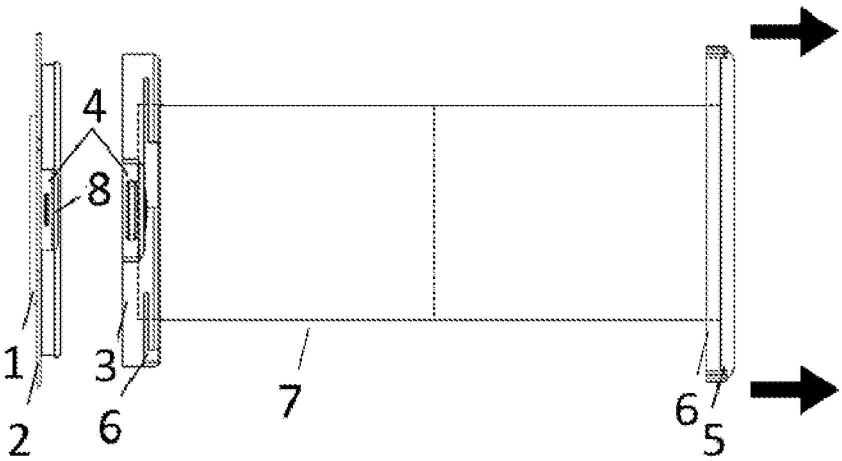
Figure 7C:
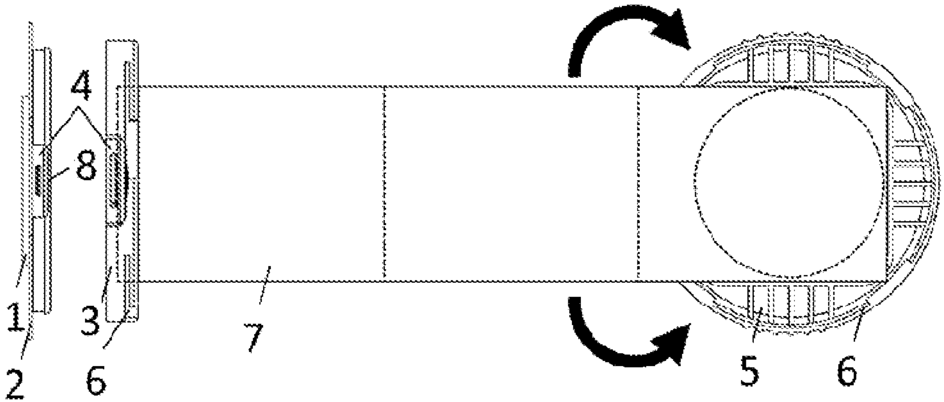
Figure 7D:
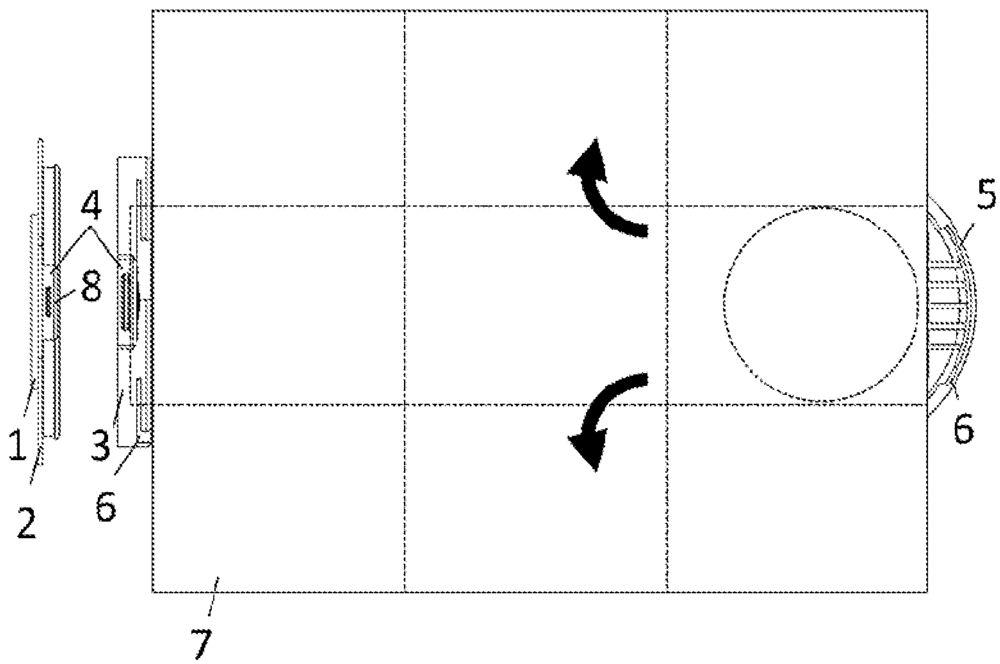

In an embodiment, the expansion of the folded compact collecting bag 7 is expedited by the folding method used to fold said collecting bag 7. When the cap 5 is manually removed, and as the faecal content reaches the bag folds, said folds loosen and facilitate the bag expansion and the flow of the faecal content from the stoma 10 into the collecting bag 7. In an embodiment, the collecting bag 7 can be folded using different configurations, such as accordion folding, twisted accordion folding (FIG. 2), zig-zag folding (FIG. 7A and FIG. 7B), folding perpendicularly and longitudinally to the length axis of the bag (FIG. 7C and FIG. 7D), or crumpled between the second base plate 3 and the cap piece 5 (FIG. 6).

For the scope of the present disclosure, the accordion folding method uses a series of alternating folds to create multiple panels of a similar size. The parallel pleats formed by the alternating folds resemble the expandable mid-section of an accordion musical instrument.

In an embodiment, the ostomy device can be used to control the release of intra-abdominal gas from the intra-abdominal cavity to the exterior. To release the gas, the valve 4 must be pressed in a movement towards the skin of the user. Contrary to the state of the art, where the valve is opened by a push movement towards the stoma, the push movement towards the abdominal skin is less harmful and more convenient for the patient. The later causes less trauma at the abdomen, in particular to the stoma, as there is no risk of applying to much force in the direction of the stoma.

In an embodiment, the valve 4 comprises a degassing aperture 8 comprising: a first channel 11 for gas flow from the stoma through the first base plate 2; a valve member 12 for opening or closing said valve and for gas flow from the first channel; and a second channel 14 for gas flow from said valve member 12 through the second base plate 3 into the exterior. Thus, a degassing aperture 8 is formed through first channel 11, the first base plate 2, through the valve member 12, through the second channel 14 through the second base plate 3 to the exterior, for gas flow from the stoma. In an embodiment, the degassing aperture 8 comprises an odour filter, an elastomeric barrier, or combinations thereof, that neutralize the potentially bad odours that may be released.

Figure 8:
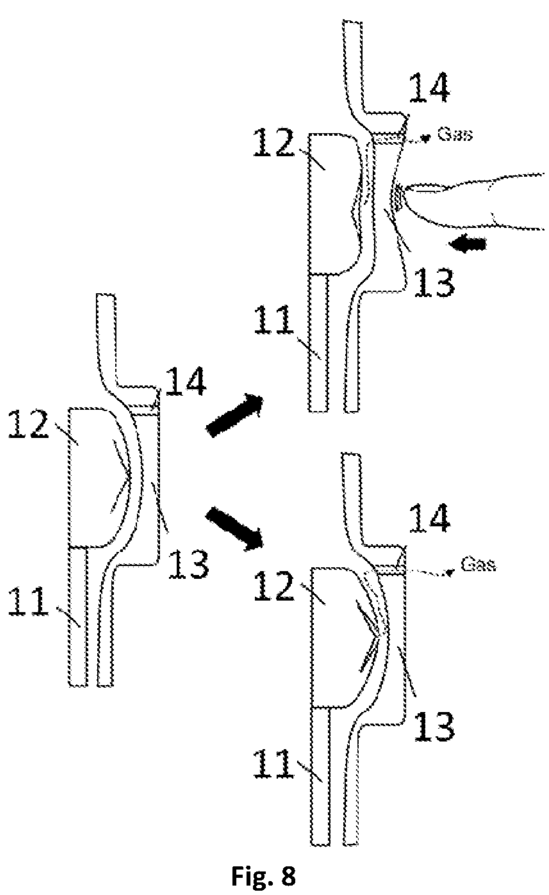
FIG. 8 shows an embodiment of the valve for releasing intra-abdominal gas into an exterior of the device.

FIG. 8 shows an embodiment of the valve 4 for releasing intra-abdominal gas into an exterior of the device. In an embodiment, the valve is connected to the space in between the stoma and the collecting bag through a valve connection channel 12. The gas flow from the stoma to the exterior of the device is interrupted by a slit membrane 12. In an embodiment, the gas can be released by an external pressure exerted by the user on the degassing button 13, that opens the membrane slit and allows the gas flow to the exterior through the degassing channel 15. In another embodiment, the gas is released by the pressure of gas generated by internal physiologic activity, that forces the slit to open, causing the gas flow from the valve to the exterior via the channel 15.

In an embodiment, the valve member 12 is a flexible membrane, wherein said membrane has a slit which is openable by pressure applied at the degassing button 13, towards the skin that surrounds the stoma 10. Therefore, when pressed, the valve allows the release of intra-abdominal gas that is release from the stoma 10 and routed through said channels 11, 14 from the first base plate 2 to the exterior (FIG. 8).

In another embodiment, the membrane slit is openable by pressure generated by internal physiological activity, causing the gas release from the valve to the exterior though channel 14.

In an embodiment, the medical device comprises a pressure sensor, that helps the ostomized subject to monitor the pressure inside the medical device. Once the intestinal content starts exerting pressure, predetermined to safe and adequate pressure values, the sensor inside the device activates an electronic alert (vibratory, sonorous or bright sign), synchronised with, for example, a smartphone app, that informs the patient about the need to go to an appropriate place for releasing the intestinal content.

In an embodiment, the relief of intestinal pressure, which may be due to faeces or gases, can be distinguished in two different ways, depending on the reason for the sensor activation.

In an embodiment, the first base plate 2 comprises a skin-contacting face for surrounding the stoma. Said skin-contacting face preferably comprises a sponge, a gaze, a cotton, or combinations thereof, to ensure a comfortable feeling to the ostomized patient.

In an embodiment, the first base plate 2 is attached to the body skin by an adhesive layer.

In an embodiment, the first and second base plates 2, 3 are attached by a flange, a snap-fit mechanism or combinations thereof.

In an embodiment, the collapsible collecting bag 7 is an ostomy bag. In another embodiment, the collapsible collecting bag is a colostomy bag, an ileostomy bag, an urostomy bag, a trachea bag, or combinations thereof, according to the final application of the medical device. In a further embodiment, the collapsible collecting bag 7 is a compact ostomy bag. In another embodiment, the collapsible collecting bag is a compact colostomy bag, a compact ileostomy bag, a compact urostomy bag, a compact trachea bag, or combinations thereof.

In an embodiment, the collapsible collecting bag 7 is disposable and/or biodegradable.

In an embodiment, the collecting bag 7 is attached to the second base plate 3 by heat sealing, suitable glue, a magnetic system, a snap-fit mechanism, an adhesive, ultrasound, or combinations thereof.

In an embodiment, the collecting bag 7 is attached to the cap 5 by heat sealing, suitable glue, a magnetic system, a snap-fit mechanism, an adhesive, ultrasound or combinations thereof.

In a further embodiment, the medical device of the present disclosure may further comprise a temperature sensor, a gas sensor, or combinations thereof.

In an embodiment, the base plates 2, 3, the valve 4 and the cap piece 5 are made of a suitable polymer, preferably polyethylene (PE), polyoxymethylene (POM), VERSAFLEX™ thermoplastic elastomer, polyesters, polyamide, polyurethane, polyethylene copolymers, silicone, or mixtures thereof.

The present disclosure also describes an ostomy system comprising the ostomy device described in any of the present embodiments, preferably wherein the ostomy system is a colostomy pouch, an ileostomy pouch, an urostomy pouch, a trachea pouch, or combinations thereof.

In an embodiment, the ostomy device described in the present disclosure is totally removable, washable and sterilizable, so that the user can clean it whenever necessary.

The term "comprising" whenever used in this document is intended to indicate the presence of stated features, integers, steps, components, but not to preclude the presence or addition of one or more other features, integers, steps, components or groups thereof.

It will be appreciated by those of ordinary skill in the art that unless otherwise indicated herein, the particular sequence of steps described is illustrative only and can be varied without departing from the disclosure. Thus, unless otherwise stated the steps described are so unordered meaning that, when possible, the steps can be performed in any convenient or desirable order.

The disclosure should not be seen in any way restricted to the embodiments described and a person with ordinary skill in the art will foresee many possibilities to modifications thereof. The above described embodiments are combinable. The following claims further set out particular embodiments of the disclosure.

The invention claimed is:

1. An ostomy device for manually controlling the release and collection of bodily waste from an external stoma of a subject, comprising:

a collapsible collecting bag;

a first base plate for encircling the stoma and for placing directly on the subject skin that surrounds the stoma;

a second base plate having an opening and connected to the collecting bag such that bodily waste can flow through the first base plate and the opening of the second base plate into the collecting bag;

a valve for releasing intra-abdominal gas into an exterior of the device; and a cap for closing and for opening the device comprising an inward side for closing onto the second base plate;

wherein the valve comprises a valve member for closing said valve, wherein the valve member is a flexible membrane having a slit which is openable by pressure applied by a hand or a finger of the subject, in a direction towards the subject skin;

wherein the valve comprises a degassing aperture comprising a first channel, a second channel, and the valve member, wherein the first channel is arranged for gas flow from the stoma through the first base plate, wherein the valve member is arranged for gas flow to be routed from the first channel to the second channel, wherein the second channel is arranged for gas flow from said valve member through the second base plate into the exterior, and wherein the first channel is arranged to be placed in parallel to the subject skin and the second channel is arranged to be placed perpendicularly to the subject skin.

2. The device according to claim 1, wherein the cap is manually removable from the second base plate.

3. The device according to claim 2, wherein the valve member is arranged to be openable by the applied pressure to release intra-abdominal gas into the exterior of the device when the cap is closed onto the second base plate.

4. The device according to claim 1, wherein the valve member is a flexible membrane having a slit which is openable by pressure applied in the direction towards the skin that surrounds the stoma.

5. The device according to claim 1, wherein the valve member is a flexible membrane having a slit which is openable by pressure of gas generated by internal physiological activity of the subject.

6. The device according to claim 1, wherein the collecting bag comprises a first end with an opening attached to an outward side of the second base plate and a second end attached to the inward side of the cap for expanding the collecting bag when the cap is manually removed from the second base plate.

7. The device according to claim 1, wherein the collapsible collecting bag is foldable and folded, and wherein the folds of the folded collecting bag loosen upon cap manual removal for expediting the fill of the collecting bag.

8. The device according to claim 1, wherein the collecting bag is folded in an accordion folding, twisted accordion folding, zig-zag folding, folding perpendicularly and longitudinally to the length axis of the bag, or crumpled.

9. The device according to claim 1, wherein the first base plate comprises a skin-contacting face for surrounding the stoma, and wherein the skin-contacting face comprises a sponge, a gaze, a cotton, or combinations thereof.

10. The device according to claim 1, wherein the first and second base plates are attachable by a flange, a screw thread, a snap-fit mechanism or combinations thereof.

11. The device according to claim 1, wherein the collapsible collecting bag is disposable and/or biodegradable.

12. The device according to claim 1, wherein the second base plate and the cap are arranged for locking the collecting bag between the second base plate and the cap, by rotation between the second base plate and the cap.

13. The device according to claim 1, wherein the collecting bag is attached to the second base plate by heat sealing, a suitable glue, a magnetic system, a snap-fit mechanism, an adhesive, ultrasound or combinations thereof.

14. The device according to claim 1, wherein the collecting bag is attached to the cap by heat sealing, a suitable glue, a magnetic system, a snap-fit mechanism, an adhesive, ultrasound, or combinations thereof.

15. The device according to claim 1, further comprising a pressure sensor, an alert system, a power source and a data processor for monitoring the intra-abdominal pressure.

16. The device according to claim 1, further comprising a temperature sensor, a gas sensor, or combinations thereof.

17. The device according to claim 1, wherein the base plates (2,3), the valve and the cap are made of a suitable polymer, preferably polyethylene, polyoxymethylene, thermoplastic elastomer, polyesters, polyamide, polyurethane, polyethylene copolymers, silicone, or mixtures thereof.

18. An ostomy system, comprising:

an ostomy device for manually controlling the release and collection of bodily waste from an external stoma of a subject, the ostomy device comprising:

a collapsible collecting bag;

a first base plate for encircling the stoma and for placing directly on the subject skin that surrounds the stoma;

a second base plate having an opening and connected to the collecting bag such that bodily waste can flow through the first base plate and the opening of the second base plate into the collecting bag;

a valve for releasing intra-abdominal gas into an exterior of the device; and a cap for closing and for opening the device comprising an inward side for closing onto the second base plate;

wherein the valve comprises a valve member for closing said valve, wherein the valve member is a flexible membrane having a slit which is openable by pressure applied by a hand or a finger of the subject, in a direction towards the subject skin, wherein the valve comprises a degassing aperture comprising a first channel, a second channel, and the valve member, wherein the first channel is arranged for gas flow from the stoma through the first base plate, wherein the valve member is arranged for gas flow to be routed from the first channel to the second channel, wherein the second channel is arranged for gas flow from said valve member through the second base plate into the exterior, and wherein the first channel is arranged to be placed in parallel to the subject skin and the second channel is arranged to be placed perpendicularly to the subject skin; and one or more pouches selected from the group consisting of: a colostomy pouch, an ileostomy pouch, an urostomy pouch, a trachea pouch, and combinations thereof.

* * * * *